United States Patent [19]

Jacobson

[11] Patent Number: 5,032,135
[45] Date of Patent: Jul. 16, 1991

[54] BOOT FOR PEG LEG

[76] Inventor: Arthur C. Jacobson, P.O. Box 83331, Portland, Oreg. 97283

[21] Appl. No.: 558,654

[22] Filed: Jul. 25, 1990

[51] Int. Cl.$^5$ .................... A61F 2/74; A45B 9/04; A61H 3/02
[52] U.S. Cl. ............................ 623/27; 623/53; 135/77; 135/86; 135/65
[58] Field of Search .................. 623/27, 32, 33, 38, 623/53, 55; 135/65-68, 70, 77-79, 82, 84, 86

[56] References Cited

U.S. PATENT DOCUMENTS

| | | | |
|---|---|---|---|
| 428,220 | 5/1890 | O'Connor | 623/29 |
| 553,929 | 2/1896 | O'Connor | 623/29 |
| 875,482 | 12/1907 | Wyatt | 623/32 |
| 1,007,730 | 11/1911 | Pozzi | 135/86 |
| 1,356,251 | 10/1920 | Willis | 623/29 |
| 2,159,301 | 5/1939 | Upton | 135/67 |
| 2,684,487 | 7/1954 | Hansen et al. | 623/27 |
| 2,689,351 | 9/1954 | Schindler | 623/33 |
| 3,461,464 | 8/1969 | Lindgren | 623/32 X |
| 3,741,226 | 6/1973 | Urban | 135/86 X |
| 4,180,872 | 1/1980 | Chaikin | 623/55 |
| 4,459,709 | 7/1984 | Leal et al. | 623/27 X |
| 4,517,688 | 5/1985 | May et al. | 623/27 |
| 4,735,754 | 4/1988 | Buckner | 623/27 X |
| 4,924,894 | 5/1990 | Martinez | 623/33 X |

FOREIGN PATENT DOCUMENTS

| | | | |
|---|---|---|---|
| 358816 | 9/1922 | Fed. Rep. of Germany | 623/27 |
| 702961 | 2/1941 | Fed. Rep. of Germany | 623/27 |

Primary Examiner—Ronald Frinks
Attorney, Agent, or Firm—Klarquist, Sparkman, Campbell, Leigh & Whinston

[57] ABSTRACT

A boot for a peg leg comprises a circular sole of non-skid elastic material, connected by a watertight seam, to a tubular upper. The upper, which is also made of an elastomeric material, is shaped to receive the shaft of a peg leg, such that the boot is held in place by friction.

12 Claims, 1 Drawing Sheet

U.S. Patent  July 16, 1991  5,032,135
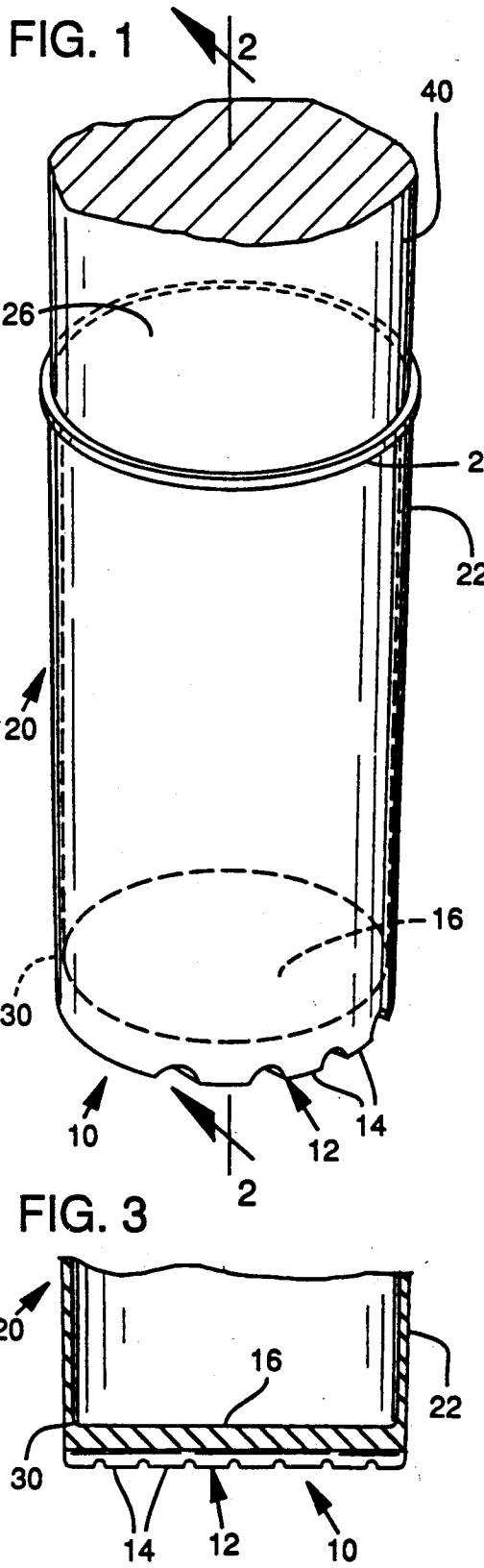
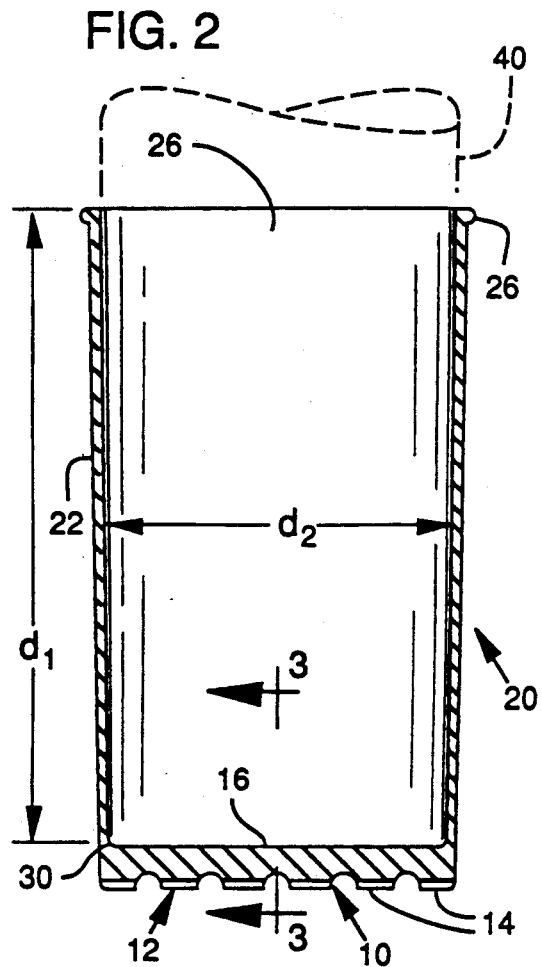
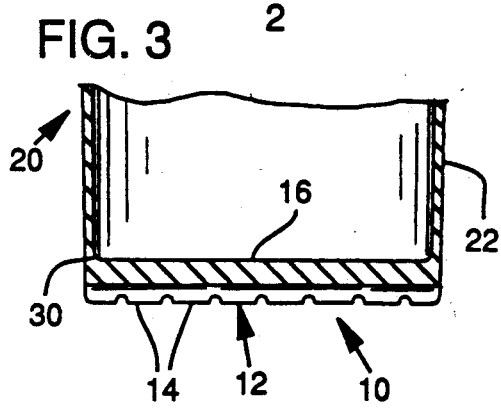
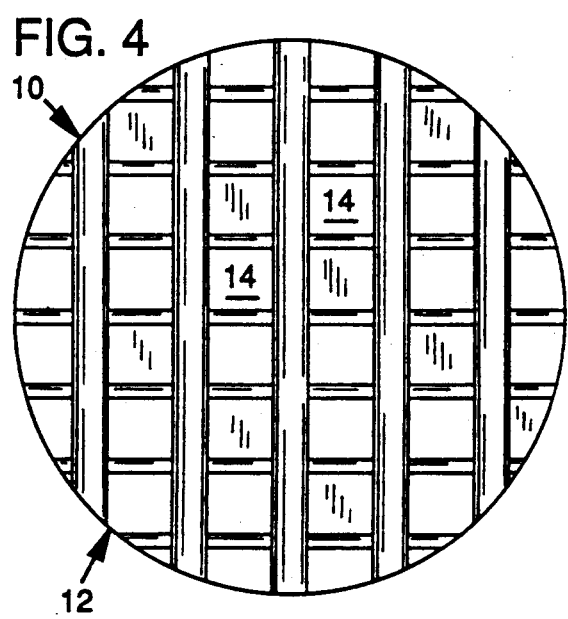

BOOT FOR PEG LEG

BACKGROUND OF THE INVENTION

The present invention relates to boots for amputees.

In recent years, numerous advances have been made in the design of prosthetic legs which simulate natural legs in appearance. Many amputees, however, still wear peg legs. Peg legs are particularly convenient when working outdoors on uneven ground. In such circumstances, it is easier to maintain one's balance and more comfortable to wear a peg leg than other prosthetic devices.

A peg leg typically consists of a shaft of circular cross-section, with a device to attach the shaft to the wearer's body. The shaft, which is most commonly made of wood, terminates at a distal end which contacts the ground when in use.

The prosthesis shown in U.S. Pat. No. 4,459,709 (Leal, et al.) has a rubber foot at the distal end of a peg made of PVC pipe. But, most peg legs have a wooden terminus, which can become slippery when wet and is subject to wear.

U.S. Pat. No. 4,517,688 (May, et al.) shows an artificial leg for a person who has had an amputation at the shin. But, the May, et al. device is not suitable for wear over a peg leg.

SUMMARY OF THE INVENTION

It has now been discovered that peg legs can be more functional, if supplied with a boot comprising a disc shaped sole with a non-skid surface and a generally cylinder upper which slips over the shaft of the peg leg, with the upper being designed for frictional contact with the shaft.

BRIEF DESCRIPTION OF THE DRAWINGS

In the drawings,

FIG. 1 is a perspective view showing a boot according to the present invention being worn on a peg leg.

FIG. 2 is a sectional view taken along plane 2—2 of FIG. 1.

FIG. 3 is a partial sectional view taken along line 3—3 of FIG. 2.

FIG. 4 is a bottom plan view of the boot shown in FIG. 1.

DETAILED DESCRIPTION

A boot includes a disc-shaped sole portion 10, having a lower surface 12 which is composed of multiple ribs or dimples 14 to provide a non-skid lower surface. The bottom of the sole 10 is preferably made of an elastomeric material, which has a high coefficient of friction.

An upper 20 extends upwardly from the sole and is likewise of generally circular cross-section. The upper 20 is a single, thin, generally cylindrical wall 22 made of an elastomeric material which can stretch to receive a peg leg and which has a high coefficient of friction.

A bead 26 around the top of the upper rigidifies the wall of the upper 20 around an opening 26, which is defined by the wall of the upper.

The wall of the upper 20 is attached to the sole 10 at a region of intersection 30. The upper and sole could be joined with a watertight seam. But, most conveniently, the upper 20 and the sole 10 are formed by integrally molding the entire boot from an elastomeric material. A mold is treated with a silicon release agent. Then, polyester liquid thermosetting castable urethane is injected. The casting is cured at 230° F. for 16 hours.

To use the boot, the wearer of a peg leg can insert the shaft 40 of the leg into the mouth 26 of the upper 20 and pressed down until it rests on the inner surface 16 of the sole 10.

The circumference of the upper 20 is selected to be slightly less than the circumference of the peg, so that the boot will be held in place by a frictional contact between the upper and the shaft 40. This is accomplished by providing an upper with an inside circumference slightly less than the circumference of the shaft.

To provide sufficient surface area for frictional contact, the upper 20 extends from the sole 12 a greater distance $d_1$ than the average diameter $d_2$ of the upper 20.

The wall of the upper 20 is a thin layer so that the boot does not substantially increase the diameter of the peg.

The upper 20 has an interior surface that can be tapered from its mouth to ease insertion of the shaft 40 and to conform to the shape of certain tapered shafts. The degree of taper should normally be quite small for a cylindrical peg shaft. A greater degree of taper can be provided to accommodate peg leg shafts that are noncylindrical.

Removal of the boot is accomplished simply by pulling it off the shaft.

The outside circumference of the boot, including the sole, does not substantially exceed the circumference of the shaft. In particular, no portion of the sole 10 extends radially outwardly of the upper 20. The boot, thus, does not alter the size or shape of the surface which contacts the ground to any substantial degree. The wearer has no trouble adapting to use of the boot, since it does not alter the characteristics of the peg, except to elevate it slightly and provide a non-skid lower surface. Because no portion of the sole or the upper extends outwardly, the boot does not impede the donning, wearing, or removal of normal clothing and cannot hook on or be caught in vines, shrubbery or the like When walking outdoors.

Because it is held in place by friction, the boot can be easily removed for a cleaning and replaced, without the use of fasteners or tools.

The boot is especially well suited for use in wet areas, with the sole and upper being made of impervious materials and being water tightly joined at the region 30. Usefulness in wet areas is further enhanced by an upper which is at least as tall as the circumference of the sole. This not only ensures good frictional fit, but also protects the shaft 40 from contact with water, should the wearer sink into muddy soil.

Having illustrated and described the principles of the present invention, it should be a-parenpt to those of ordinary skill in the art that such embodiments may be modified in detail without departing from such principles. I claim as my invention all such modifications as come within the true spirit and scope of the following claims.

I claim:

1. A boot for a peg leg, the boot comprising:
   a sole; and
   an upper which is a single, thin wall, is attached to and extends upwardly from the sole to a distal end which defines a mouth, is made of a flexible material, is substantially tubular, is a substantially circular ring in cross-section, extends from the sole a greater distance than the diameter of the ring, and has an interior surface which tapers from the mouth to the region where the sole and the upper are joined.

2. The boot of claim 1, wherein the sole is substantially planar and has a lower non-skid surface.

3. The boot of claim 1, wherein the sole is flexible, but self-supporting.

4. The boot of claim 1, wherein the sole is disc-shaped.

5. The boot of claim 1, wherein the upper is a wall that extends upwardly from the perimeter of the sole, such that no portion of the sole extends beyond the region defined by the wall.

6. The boot of claim 1, wherein the upper is made of a flexible material.

7. The boot of claim 1, wherein the upper is substantially a tube with an axis that is normal to the sole.

8. The boot of claim 1, wherein the upper has a circumference substantially large enough, such that the upper can stretch to receive a peg leg of generally circular cross-section and small enough that friction between the peg leg and the upper will hold the boot in place.

9. The boot of claim 1, wherein the upper is substantially of the same circumference as the sole at the region where the sole and the upper are joined, such that no portion of this sole extends beyond the region defined by the upper.

10. The boot of claim 1, wherein the upper extends from the sole and terminates at an end, distal from the sole, where the upper defines an opening to receive a peg leg of generally circular cross-section.

11. The boot of claim 10, wherein the upper has a thickened portion at the end to rigidify the upper at the region at the opening.

12. A boot for a peg leg of generally circular cross-section, the boot comprising:

a sole which (a) is a planar sheet of material having a lower, non-skid tread surface, (b) is flexible, but self-supporting, and (c) is disk-shaped; and an upper which (a) is a single, thin wall that is joined to and extends upwardly from the perimeter of the sole, such that no portion of the sole extends beyond the region defined by the wall, (b) is made of a flexible material, (c) is substantially a tube with an axis that is normal to the sole, (d) is a substantially circular ring in cross-section with a circumference large enough that the upper can stretch to receive a peg leg of a generally circular cross-section and small enough that friction between the peg leg and upper will hold the boot in place, (e) is substantially of the same circumference as the sole at the region where the sole and the upper are joined, (f) flares from the region where the sole and the upper are joined, (g) extends from the sole a greater distance than the diameter of the ring, (h) terminates at an end, distal from the sole, where the wall defines an opening to receive the peg leg and (i) has a thickened portion at the end to rigidify the upper at the region of the opening.

* * * * *